United States Patent
Smith

[11] Patent Number: 6,146,392
[45] Date of Patent: Nov. 14, 2000

[54] NEEDLE HOLDING AND MANIPULATING INSTRUMENT

[76] Inventor: Stephen B. Smith, 917 Rabbit Run, Wilmington, N.C. 28409

[21] Appl. No.: 09/433,270

[22] Filed: Nov. 3, 1999

[51] Int. Cl.[7] .................................................. A61B 17/04
[52] U.S. Cl. ............................................. 606/147; 606/145
[58] Field of Search ..................................... 606/145–147

[56] References Cited

U.S. PATENT DOCUMENTS

| | | |
|---|---|---|
| 3,139,089 | 6/1964 | Schwerin . |
| 3,168,097 | 2/1965 | Dormia . |
| 3,638,654 | 2/1972 | Akuba ..................... 606/147 |
| 5,201,743 | 4/1993 | Haber et al. ............. 606/147 |
| 5,224,948 | 7/1993 | Abe et al. ................ 606/147 |
| 5,282,806 | 2/1994 | Haber et al. ............. 606/147 |
| 5,540,705 | 7/1996 | Meade et al. ............ 606/147 |
| 5,556,402 | 9/1996 | Xu . |
| 5,707,379 | 1/1998 | Fleenor et al. .......... 606/147 |
| 5,843,100 | 12/1998 | Meade ..................... 606/147 |
| 5,954,733 | 9/1999 | Yoon ....................... 606/147 |
| 5,957,937 | 9/1999 | Yoon ....................... 606/147 |
| 5,993,466 | 11/1999 | Yoon ....................... 606/147 |
| 5,993,467 | 11/1999 | Yoon ....................... 606/147 |

*Primary Examiner*—Gary Jackson
*Attorney, Agent, or Firm*—Rhodes & Mason, PLLC

[57] ABSTRACT

A needle clamp is used to clamp and manipulate a suturing needle having a given radius of curvature. The clamp includes a pair of opposed arms that have an open position for insertion of the needle and a closed or clamping position. The arms are rotatable together about a rotational axis, and the needle is held in a curved convex groove positioned from the rotational axis at a distance approximately equal to the radius of curvature of the needle, so that the needle rotates about its curvature. The replaceable clamp is held along the rotational axis by an instrument handle that includes opposed clamp-engaging members, with the clamp and instrument handle having mating projections and recesses. The instrument also includes a manipulator to rotate the clamp about the rotational axis. The needle clamp may be permanently affixed on the clamp-engaging members or may be releasibly engaged such that various different needle clamps may be interchangeably affixed on the instrument handle engaging members.

20 Claims, 6 Drawing Sheets

NEEDLE HOLDING AND MANIPULATING INSTRUMENT

BACKGROUND OF THE INVENTION (1) Field of the Invention

The present invention relates generally to a hand instrument for use during surgical procedures to hold and manipulate a suturing needle, and in particular to an instrument of this type that can be used to move a surgical needle along a curved pathway.

(2) Description of the Prior Art

Surgical procedures normally require suturing or stitching of tissues to close incisions or other cuts. This suturing is performed by pushing a needle through one side of the tissue to be sutured, and grasping the needle tip on the exit side to withdraw the needle. The needle and attached suture can then be drawn through the tissue and the suture tied.

Suturing is a relatively simple procedure when performed on external tissues, since the surgeon can easily manipulate the instruments used to insert and withdraw the needle. Many surgical procedures, however, require suturing of internal tissues or organs, severely limiting the ability of the surgeon to manipulate the needle holder to push the needle through the tissue.

Several instruments are described in the prior art that purport to address this problem. The following patents are representative of prior art suturing instruments:

| U.S. Pat. No. | Inventor(s) |
| --- | --- |
| 5,843,100 | Meade |
| 3,139,089 | Schwerin |
| 5,556,402 | Xu |
| 5,540,705 | Meade et al. |
| 3,168,097 | Dormia |
| 3,638,654 | Akuba |
| 5,224,948 | Abe et al. |
| 5,282,806 | Haber et al. |
| 5,201,743 | Haber et al. |
| 5,707,379 | Fleenor et al. |

Generally, these instruments are comprised of a handle or holder that has a needle grasping member at its distal end, a means to open and close the needle grasping member, and a manipulation means to rotate the needle grasping member. The handle may be comprised of first and second members with opposed jaws that are designed to open and close the needle grasping member. In some instruments, the needle grasping member is designed to rotate about an axis that is parallel to the longitudinal axis of the handle, while the needle grasping member in other instruments rotates about an axis that is transverse to the longitudinal axis of the handle.

A representative instrument is described in U.S. Pat. No. 5,843,100 to Meade. The Meade instrument comprises a pair of scissor-like arms having distal ends, with a needle grasping member rotatably attached at a pivot point to the distal ends. This needle grasping member is comprised of opposed sections that may be clamped together to grasp the proximal end of a surgical needle at the axis of rotation of the needle grasping member. The needle grasping member is connected to a manipulation means that is used to rotate the needle grasping member, causing the tip of the needle to move along a circular path.

Prior art instruments, particularly instruments in which the needle is to be carried along a pathway with a plane of rotation parallel to the longitudinal axis of the instrument have various defects that limit their usefulness in surgical procedures. Of major concern is the fact that rotation of a needle using an instrument of the type described by Meade causes a clawing or tearing action that can damage the tissues, and also makes insertion of the needle into the tissue difficult.

Additionally, there is a tendency in many instruments for the needle to shift out of alignment when pressure is exerted to insert the needle through tissue. Proper initial alignment of the needle in the instrument under operating conditions also presents a challenge to the surgeon, or assistant. Use of the instrument to pull the needle the rest of the way through the tissue after the needle has been inserted into the tissue can also be difficult.

Another reason needle manipulating instruments have found limited acceptance is the fact that most instruments are designed to hold a needle of only one size. Needles of different sizes are used during surgery, however, necessitating the costly acquisition, and subsequent sterilization, of plural needle manipulating instruments.

The convenience to the surgeon, and the acceptance of these instruments, would be considerably improved if these problems were addressed.

SUMMARY OF THE INVENTION

The present invention is directed to a hand-held surgical instrument used to grasp a suturing needle, and move the needle along a curved pathway. Generally, the instrument is comprised of an elongated handle with distal and proximal ends, and a pair of opposed clamping jaws moveable between open and closed positions at its distal end; a rotatable needle clamp carried by the opposed jaws, and a manipulator to rotate the needle clamp.

The handle can be of various constructions. For example, a pair of pivotally attached arms of the type shown by Meade, and commonly found in forceps or needle-holders can be used. Other handles of the type used in endoscopic or laparoscopic instruments can be used. The common and relevant features of these handles is a proximal end adapted to be grasped by the surgeon, and a distal end that can be moved between an open position and a closed position.

Various manipulators can also be used to rotate the needle clamp. Basically, the manipulator should have a distal end that is connectable to the needle clamp, and a proximal end that can be reached by the surgeon to rotate the needle clamp.

The present invention differs significantly, however, in the construction of the needle clamp, and the manner in which the needle clamp is carried on the jaws of the elongated handle. As a result of these differences, to be described in detail herein, the manner in which a surgical needle is held and manipulated differs substantially from the prior art, and resolves the disadvantages observed when trying to grasp and manipulate a needle with prior art instruments.

More specifically, the needle clamp of the present invention is comprised of opposed clamping arms that have distal ends and proximal ends that are moveable between open and closed positions, so that a needle can be clamped between the arms adjacent their distal ends when in the closed position. The proximal ends of the needle clamp may be joined such that the entire needle clamp unit functions in a manner similar to a forcep, the distal tips of which grip the suture needle.

Alternatively, the needle clamp arms may have no such direct connection but may be linked together by the manipulator mechanism such that the arms always move together. The joined needle clamp arms are adapted to rotate together around a transverse rotational axis that is spaced from the point of needle engagement. This rotational axis is determined by a pivot point positioned on each clamp arm intermediately between the distal ends and the joined proximal needle clamp end. As a result, the needle is carried along a circular pathway that has a radius equal to the distance between the needle engagement point and the rotational axis.

The clamp holder is designed to hold a needle having a radius of curvature approximately equal to the radius of the defined circular pathway. Thus, when the needle is held transverse to the longitudinal axis of the needle arms, all parts of the needle will be carried along a circular pathway closely approximating the curvature of the needle. As a result, the clawing action experienced with prior art devices, and the resultant trauma to the patient, is avoided.

In order to ensure proper placement of the needle between the clamping arms, and to minimize shifting of the needle during use, the arms preferably have facing curved, needle-alignment grooves or slots on their inner surfaces. When the arms are in their closed position, these needle-alignment grooves form a curved needle-receiving channel with a curvature substantially equal to the curvature of the surgical needle to be used with the needle clamp. This channel is positioned along the aforementioned circular pathway, and has a radius of curvature equal to the distance between the channels and the rotational axis of the clamp.

The needle clamp is connected to the above-described manipulator so that movement of the manipulator causes the clamp to rotate about its pivot point. The manner in which the clamp is attached to the manipulator can take various forms, depending upon the construction of the clamp. For example, the proximal ends of the arms of the needle clamp may be connected to each other and to the manipulator by lever arms that extend at an angle from the clamping arms. The lever arms are then pivotally attached to the manipulator. Alternatively, the two needle clamp arms may be permanently fused at their proximal ends to form a single unit, with the rotation point of the needle clamp arms located more distally, such that the portion of the needle clamp arms distal to the rotation point will behave mechanically as a lever arm on the joined arm.

The clamping arms of the needle clamp are rotatably attached to the jaws of the handle and are directly or indirectly connected to each other, so that the needle clamp's jaws rotate together when the manipulator acts upon the needle clamp. That is, a first needle clamp arm is rotatably connected to a first jaw and the second arm is rotatably connected to a second jaw. These rotatable connections may be of a permanent nature. In a preferred embodiment of the invention, however, the needle clamp is releasibly connected to the handle jaws, so that different needle clamps can be used with the same handle. Thus, the needle clamp can be disposable and/or needle clamps sized to clamp needles of different sizes can be used with the same handle.

In a preferred embodiment of the invention, the needle-grasping member is formed as a single molded piece, with the proximal ends of the spaced, parallel arms being attached to angled, resilient lever arms that are joined at their proximal ends. When the lever arms are unflexed, i.e., in their open position, the clamping arms are spaced with their inner surfaces being at a given extended distance, sufficient to easily accommodate suture needle placement between the arms.

In this preferred embodiment, the lever arms are joined at their outer ends to form a connection end that includes a bore to pivotally join the needle clamp to the manipulator. Recesses or bores, referred to herein collectively as recesses, extend into or through the midportion of the clamping arms along the clamp's rotational axis to receive pins or projections that extend from the inner faces of the jaws of the handle. (Alternatively, pins could project outwardly from the needle clamp's center of rotation, to engage corresponding recesses or bores in the handle jaws. In order to hold the needle clamp in place when the handle jaws are in their open position, the distance between the inner ends of the pins when the jaws are in their most open position is less than the distance between the outer faces of the arms of the needle clamp when the needle-clamping member is in the unflexed condition. Therefore, it is necessary to force the clamping arms toward each other in order to insert the needle clamp between pins and align the pins with the recesses in the clamping arms. After insertion, the pressure on the needle clamp is removed so that the needle clamp returns to its unflexed condition, so that the clamping arms exert an outward pressure against the jaws to hold the pins or projections in the recesses.

The tendency of the needle to rotate out of alignment in the needle clamp, or to flex during insertion into tissue, can be further reduced by adding needle support shoulders to extend outwardly from one side of the arms. These shoulders have front (distal) surfaces following the radius of needle alignment grooves of the pathway, and are positioned behind the needle when the needle is in position. The needle clamp portion of the instrument is designed such that the shoulders are curved in continuity with the needle alignment grooves described earlier.

The tips of the arms, i.e., the portion of the arms between the needle grasping point and the distal end of the arms, can be used to grasp a needle after the tip of the needle has been inserted through the tissue. That is, the needle is released from the needle clamp, and the tips of the arms are then used to grasp the needle tip and pull the needle the rest of the way through the tissue. One or more small concave grooves may be formed on the inner face of each clamping arm tip to improve this grip. Alternatively, the inner faces may be textured to facilitate grasping the suture needle in this manner.

It is often necessary to replace the needle in the instrument during a surgical procedure. Ready alignment of the needle in the retaining grooves can be difficult due to the presence of fluids that cause the surfaces to become slippery and obstruct visibility. Therefore, the needle clamp may also include a guide to urge the needle into its correct position. This guide may be in the form of an angled shoulder that projects inwardly from an edge of one of the arms and over the edge of the other arm. The guide is angled rearwardly from the groove of the arm carrying the guide. Alternatively, the guide may extend transversely from an edge of one arm across the corresponding edge of the other arm. Guides may be positioned on one or both edges of the clamp. When a needle is inserted between the arms and the arms are clamped together, the guide or guides position the needle into alignment with the needle grooves.

In operation, a needle is positioned in the grooves of the needle clamp, and the clamping arms are forced together to hold the needle in the channel formed by the grooves. When using a handle comprised of two pivotal arms with jaws at their distal ends, the arms are brought together at their proximal ends and locked into the closed position.

The instrument is then positioned with the needle tip adjacent the tissue to be sutured, and the manipulator is used to rotate the needle clamp so that the needle tip is inserted through the tissue. Due to the unique configuration of the instrument, the curved needle shaft follows the pathway of the needle tip, thereby minimizing any clawing action, and minimizing resistance to insertion. After the tip of the needle has been inserted through the tissue, the needle clamp is opened to release the needle from the clamp. The tips of the needle clamp arms are then placed on opposite sides of the projecting needle tip, and clamped together to grasp the needle. The needle is then pulled through the tissue, so that the suture can be tied.

As noted earlier, the needle clamp may be disposable to reduce sterilization needs. In this embodiment, a single handle can be used with a plurality of needle clamps that are sized to accommodate surgical needles having a different size and radius of curvature. The needle clamps will differ in the distance between the clamp pivot point and the needle engagement point, so that the needles will be rotated along circular pathways having a different radius. In each instance, the radius of curvature of the given needle will approximately correspond to the radius of curvature of the defined pathway.

Accordingly, one aspect of the present invention is to provide an instrument for holding and manipulating a suturing needle having a given radius of curvature that is comprised of a handle having a longitudinal axis, and proximal and distal ends with needle clamp-engaging members; and a needle clamp having first and second needle clamping arms with inner and outer faces, the clamping arms being moveable between an open position and a closed position, the arms being rotatably supported between the clamp-engaging members along a given rotational axis, and having a needle grasping position spaced from the rotational axis, the distance between the rotational axis and the grasping position being approximately equal to the radius of curvature of the needle.

Another aspect of the present invention is to provide a needle clamp for use with a handle having a longitudinal axis, and proximal and distal ends to hold and manipulate a suturing needle having a given radius of curvature that is comprised of first and second needle clamping arms with inner and outer faces, and upper and lower edges, the clamping arms being moveable between an open position and a closed position, the arms being rotatably supportable between the handle distal ends along a given rotational axis, and having a needle grasping position spaced from the rotational axis, the distance between the rotational axis and the grasping position being approximately equal to the radius of curvature of the needle.

Still another aspect of the present invention is to provide an instrument for manipulating a replaceable needle clamp used to clamp a suturing needle having a given radius of curvature, the instrument having a longitudinal axis, the instrument being comprised of first and second opposed clamp engaging members to releasibly hold the needle clamp along an axis of rotation, first and second handles having distal ends operatively connected to the clamp engaging members to move the clamp-engaging members between open and closed positions, and proximal ends; and a manipulator having a distal end connectable to the needle clamp to rotate the clamp about the axis of rotation.

These and other aspects of the present invention will become apparent to those skilled in the art after a reading of the following description of the preferred embodiment.

DETAILED DESCRIPTION OF THE INVENTION

It will be understood that the instrument can be turned to various orientations during use. Therefore, terms such as upper, lower, and the like, are used solely for definitional purposes, and should not be taken as words of limitation. The drawings are for the purpose of illustrating the invention and are not intended to be to scale.

Figure 1:
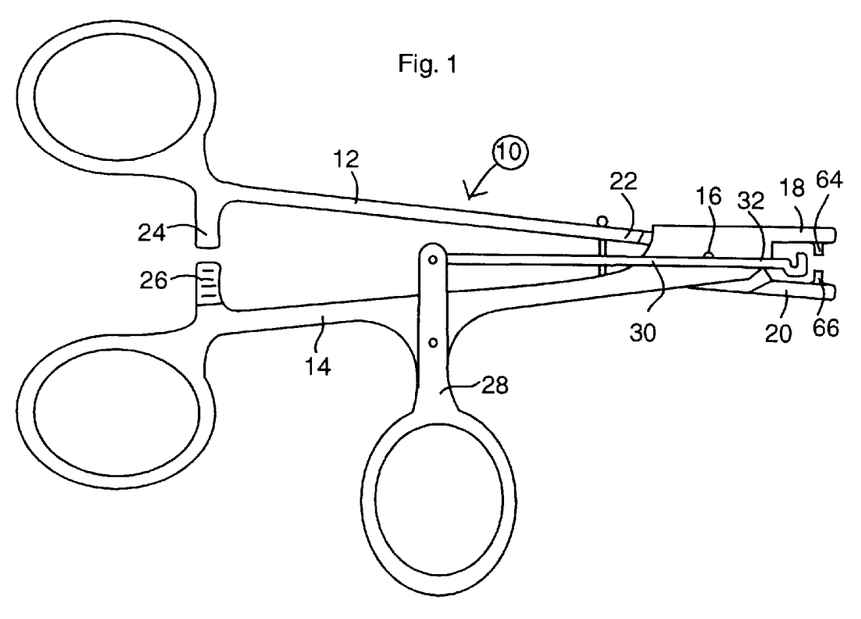
FIG. 1 is a side view of the instrument handle without a needle clamp inserted.

FIG. 1 illustrates one embodiment of a clamp holder or handle, generally 10, that can be used with a needle clamp of the type illustrated in FIGS. 2–9 to form an operable instrument of the invention primarily for use in open surgery. Handle 10 is comprised of a first member 12 and a second member 14, each having a proximal end and a distal end. Members 12 and 14 are pivotally joined to each other close to their distal ends by pivot pin 16 in a scissor-like arrangement. The distal ends of members 12 and 14 terminate in opposed clamping jaws 18 and 20, which have an open position when the proximal ends of members 12 and 14 are moved apart, and a closed position when the proximal ends of members 12 and 14 are moved together.

The opening of members 12 and 14, and thereby the distance between the opposed faces of clamping jaws 18 and 20, is limited by a stop 22. Locking sections 24 and 26 engage each other when members 12 and 14 are moved together, to hold jaws 18 and 20 in their closed position.

The needle clamp is rotated with a clamp rotator or manipulator comprised of an actuator arm 28 pivotally attached intermediate its proximal and distal ends to member 14, and an actuator rod 30 pivotally attached at its proximal end to the distal end of actuator arm 28. Rod 30 is generally longitudinally aligned with handle 10, and terminates at its distal end with clamp connector 32.

Figure 2:
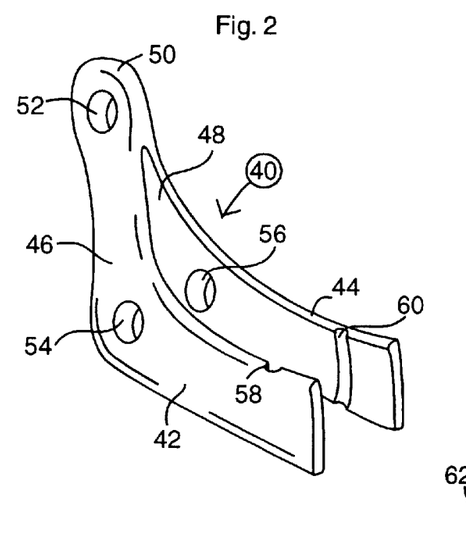
FIG. 2 is perspective view of one embodiment of a needle clamp.
Figure 3:
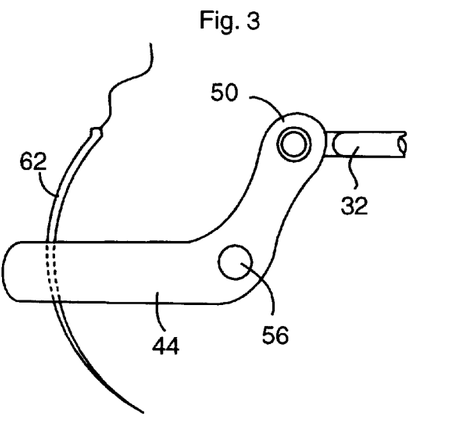
FIG. 3 is a side view of needle clamp of FIG. 2.
Figure 4:
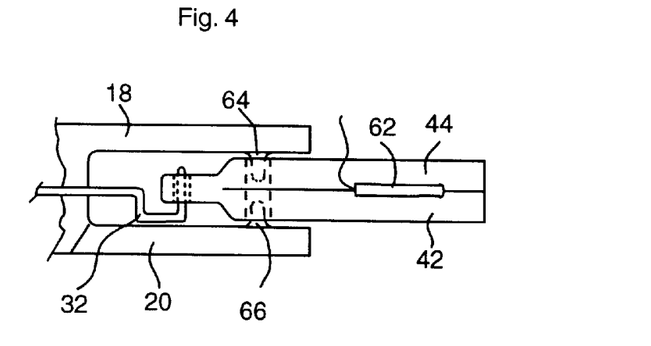
FIG. 4 is a top view of the needle clamp of FIG. 2, while closed by instrument handle jaws.
Figures 5, 6, 7, 8, 9:
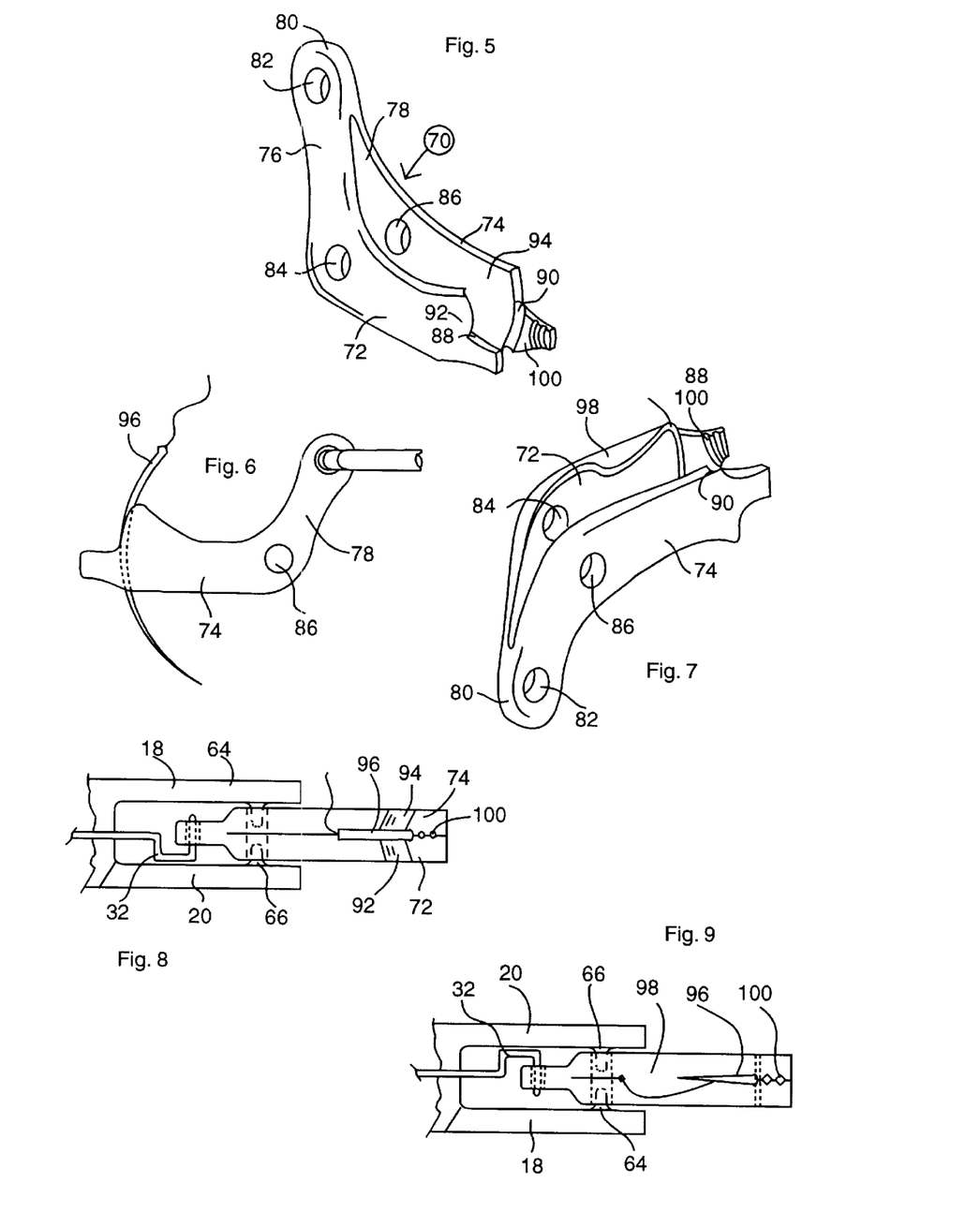
FIG. 5 is perspective view of another embodiment of a needle clamp.
FIG. 6 is a side view of needle clamp of FIG. 5.
FIG. 7 is an inverted perspective view of the needle clamp of FIG. 5.
FIG. 8 is a top view of the needle clamp of FIG. 5.
FIG. 9 is a bottom view of the needle clamp of FIG. 5.

FIGS. 2, 3 and 4 illustrate one embodiment of a needle clamp, generally 40, that can be used with handle 10. Clamp 40 is comprised of parallel clamping arms 42 and 44, each arm having inner and outer faces, and upper and lower edges. Integral lever arms 46 and 48 extend outwardly at an angle from the proximal ends of arms 42 and 44, respectively, and meet at a connecting end 50. Connecting end 50 includes a bore 52 to pivotally connect clamp 40 to clamp connector 32.

Clamping arms 42 and 44 include bores or recesses 54 and 56, respectively, along the rotational axis adjacent their proximal ends for use in pivotally connecting clamping arms 42 and 44 to clamping jaws 20 and 18, respectively. Convex needle positioning grooves 58 and 60 are formed in the inner faces of arms 42 and 44, respectively, adjacent the distal ends of arms 42 and 44. As used herein, the term "convex" means that the center of each groove projects toward the distal end of the arm.

Convex grooves 58 and 60 are positioned at a given distance from the pivot points, determined by the location of bores 54 and 56, that is equal to the radius of curvature of a needle 62 to be clamped in grooves 58 and 60. The radius of curvature of grooves 58 and 60 will be approximately equal to radius of curvature of the needle. Thus, when clamp 40 is rotated, the needle connection point will move along a circular pathway having a radius of curvature equal to the radius of curvature of the needle. Since the needle is clamped at its engagement point transverse to the axis of the arms, all parts of needle 62, i.e., the needle shaft from one end to the other, will move along the circumference of the defined circle.

Clamping jaws 18 and 20 include inwardly projecting pivot pins 64 and 66, which are releasibly inserted into bores 56 and 54, respectively, to rotatably and releasibly attach needle clamp 40 to handle 10. Clamp connector 32 is pivotally inserted into bore 52.

FIGS. 5, 6, 7, 8 and 9 illustrate an alternative embodiment of a needle clamp, generally 70, which is similar in construction to clamp 40, but with certain modifications to improve insertion and holding of a needle. Clamp 70, like clamp 40, is comprised of parallel clamping arms 72 and 74, each arm having inner and outer faces, and upper and lower edges, and integral lever arms 76 and 78 extending outwardly at an angle from adjacent the proximal ends of arms 72 and 74, respectively, to meet at connecting end 80.

Connecting end 80 includes a bore 82 to pivotally connect clamp 70 to clamp connector 32. Clamping arms 72 and 74 include bores 84 and 86, respectively, adjacent their proximal ends to pivotally connecting clamping arms 72 and 74 to clamping jaws 20 and 18, respectively. Convex needle positioning grooves 88 and 90 are formed in the inner faces of arms 72 and 74, adjacent their distal ends, with the distance between the grooves and the bores, i.e., the pivot points, being equal to the radius of curvature of the needles to be held in clamp 70.

Clamp 70 additionally includes needle support shoulders 92 and 94 that project outwardly from the upper side of each arm 72 and 74, respectively, immediately behind grooves 88 and 90. Shoulders 92 and 94 have front, rearwardly curved and inwardly angled faces that together form a curved trough or groove against which needle 96 is positioned when needle 96 is inserted into the channel formed by grooves 88 and 90. The additional support provided by shoulders 92 and 94 aids in resisting flexing or twisting of needle 96 when needle 96 is pushed into tissue.

Clamp 70 also includes a curved needle guide 98 that projects inwardly from an edge of arm 72, and over the corresponding edge of arm 74 when the arms are clamped together. Guide 98 curves outwardly from immediately behind groove 88. When needle 96 is inserted between arms 72 and 74, guide 98 forms an angle with the inner wall of arm 74, which tends to force needle 96 toward and into grooves 88 and 90, thereby aiding in the proper seating of needle 96.

Figure 10:
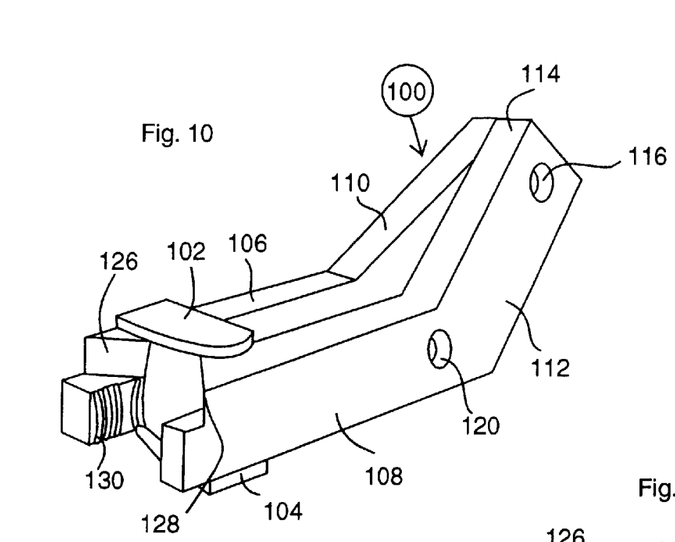
FIG. 10 is a perspective view of yet another embodiment of a needle clamp.
Figure 11:
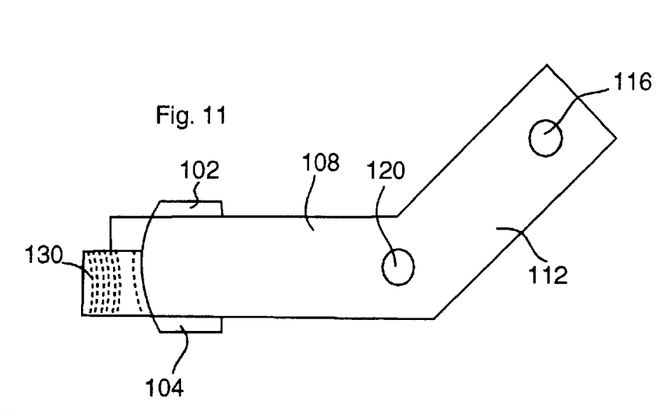
FIG. 11 is a side view of needle clamp of FIG. 10.
Figure 12:
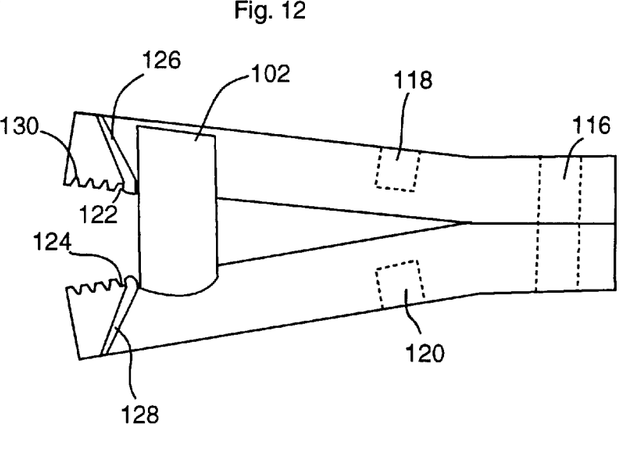
FIG. 12 is a top view of the needle clamp of FIG. 10.

Yet another needle clamp is illustrated in FIGS. 10–12. This needle clamp, generally 100, differs primarily in construction from clamp 70 in the positioning of needle guides 102 and 104. Clamp 100 is comprised of parallel clamping arms 106 and 108, each arm having inner and outer faces, and upper and lower edges, and integral lever arms 110 and 112 extending outwardly at an angle from adjacent the proximal ends of arms 106 and 108, respectively. The proximal ends of arms 106 and 108 are fused together to form a connecting end 114.

Connecting end 114 includes a bore 116 to pivotally connect clamp 100 to clamp connector 32. Clamping arms 106 and 108 include bores 118 and 120, respectively, adjacent their proximal ends to pivotally connect clamping arms 106 and 108 to a handle or operating instrument. Convex needle positioning grooves 122 and 124 are formed in the inner faces of arms 106 and 108, adjacent their distal ends, with the distance between the grooves and the bores, i.e., the pivot points being equal to the radius of curvature of the needles to be held in clamp 100.

Clamp 100 additionally includes needle support shoulders 126 and 128 that project outwardly from the upper side of each arm 106 and 108, respectively, immediately behind grooves 122 and 124. Shoulders 126 and 128 have front, rearwardly curved and inwardly angled faces that together form a curved trough or groove against which a needle is positioned when inserted into the channel formed by grooves 122 and 124. The inner faces of the tips of arms 106 and 108 also include concave grasping grooves 130 to aid in grasping the tip of the needle after the needle has been inserted through the tissue, so that the needle can be pulled through the tissue.

Needle guides 102 and 104 project inwardly from opposite edges of clamping arms 106 and 108, respectively, immediately behind shoulders 126 and 128, and extend across the corresponding edge of the opposite arm. Thus, when a needle is inserted between the inner faces of arms 106 and 108, the needle will engage shoulders 126 and 128, thereby aligning the needle with needle grooves 122 and 124. It will be understood that other embodiments may only use one needle guide.

FIGS. 13–16 illustrate a laproscopic instrument, generally 140, that incorporates the features of the invention. Instrument 140 is comprised of proximal handles 142 and 144 that can be locked together with ratchet closure 146, and an elongated solid support member 148 that is continuous down the length of the instrument. First and second drive bars 150 and 152, respectively, are positioned adjacent opposite sides of support member 148. The outer surfaces of the proximal ends of bars 150 and 152 include gear teeth 154 that are engaged by inner gear teeth 156 on the distal ends of handles 142 and 144, respectively.

First and second identical clamping jaws 158 are pivotally attached to the distal ends of drive bars 150 and 152. Each clamping jaw includes in inwardly directed clamp attachment pin 160, a distal pivotal attachment 162 for drive bar 150 or 152, and a pivotal attachment 164 to join jaws 158 to the distal end of support member 148. In the embodiment illustrated, attachment 164 is intermediate attachment pin 160 and attachment 162. A sheath 166 surrounds member 148 and bars 150 and 152, for insertion of the instrument through a trocar.

Instrument 140 further includes a manipulator bar handle 168 pivotally attached to handle 142, and a manipulator 170 extending along the longitudinal axis of support member 148. The proximal end of manipulator 170 is pivotally attached to the distal end of handle 168, while the distal end of manipulator 170 includes a releasible attachment member to pivotally secure the end of manipulator 170 to a needle clamp, shown in the drawings as needle clamp 100.

When the instrument handle of FIG. 1 is to be used, members 12 and 14 of handle 10 are opened to the open position, and a needle clamp is inserted between jaws 18 and 20. The following description will refer to clamp 40. However, it will be understood that the same steps are followed with clamp 70 or 100.

Due to stop 22, the maximum open distance between the inner tips of pins 64 and 66 is less than the distance between the outer faces of clamping arms 42 and 44. Therefore, the user presses arms 42 and 44 toward each other when inserting clamp 40 and aligns pins 64 and 66 with bores 54 and 56. Clamp 40 is then released, allowing arms 42 and 44 to expand toward jaws 18 and 20, where they are rotatably supported on pins 64 and 66. Clamp connector 32 is also pivotally attached through bore 52.

A needle is then inserted between the inner faces of clamp arms 42 and 44, and members 12 and 14 are closed to clamp needle 62 into a channel formed by grooves 58 and 60. Thus, when actuator arm 28 is pulled in toward the user, actuator rod 30 is pushed toward the distal end of handle 10, rotating clamp 40 around pins 64 and 66, to move needle 62 along a circular pathway.

Figures 13, 14, 15:
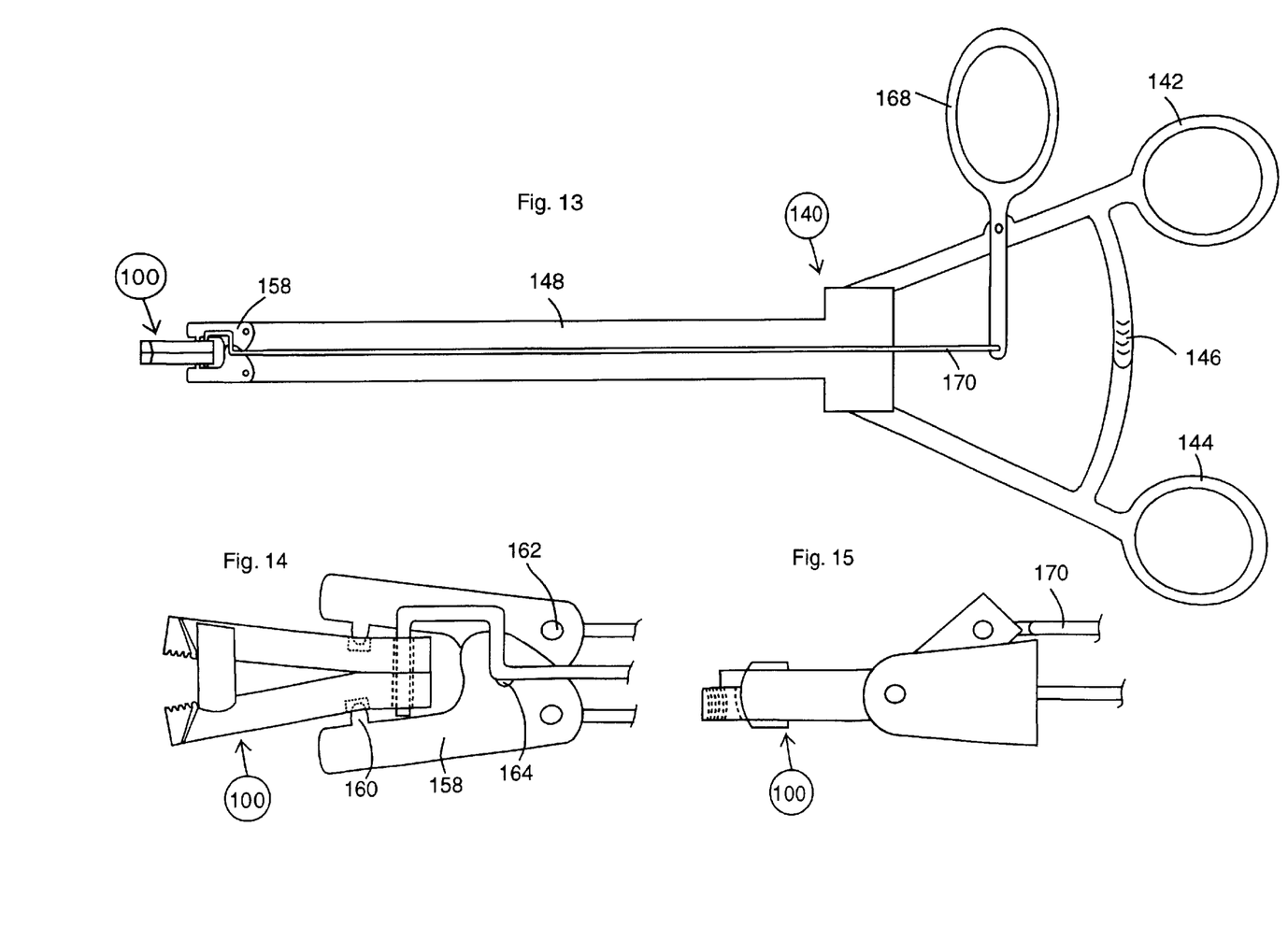
FIG. 13 is a top view of a laparoscopic instrument incorporating the feature of the invention with the needle clamp of FIG. 10 in a closed position.
FIG. 14 is a detailed top view of the distal end of the instrument of FIG. 13, with the needle clamp in an open position.
FIG. 15 is a detailed side view of the distal end of the instrument of FIG. 13.
Figure 16:
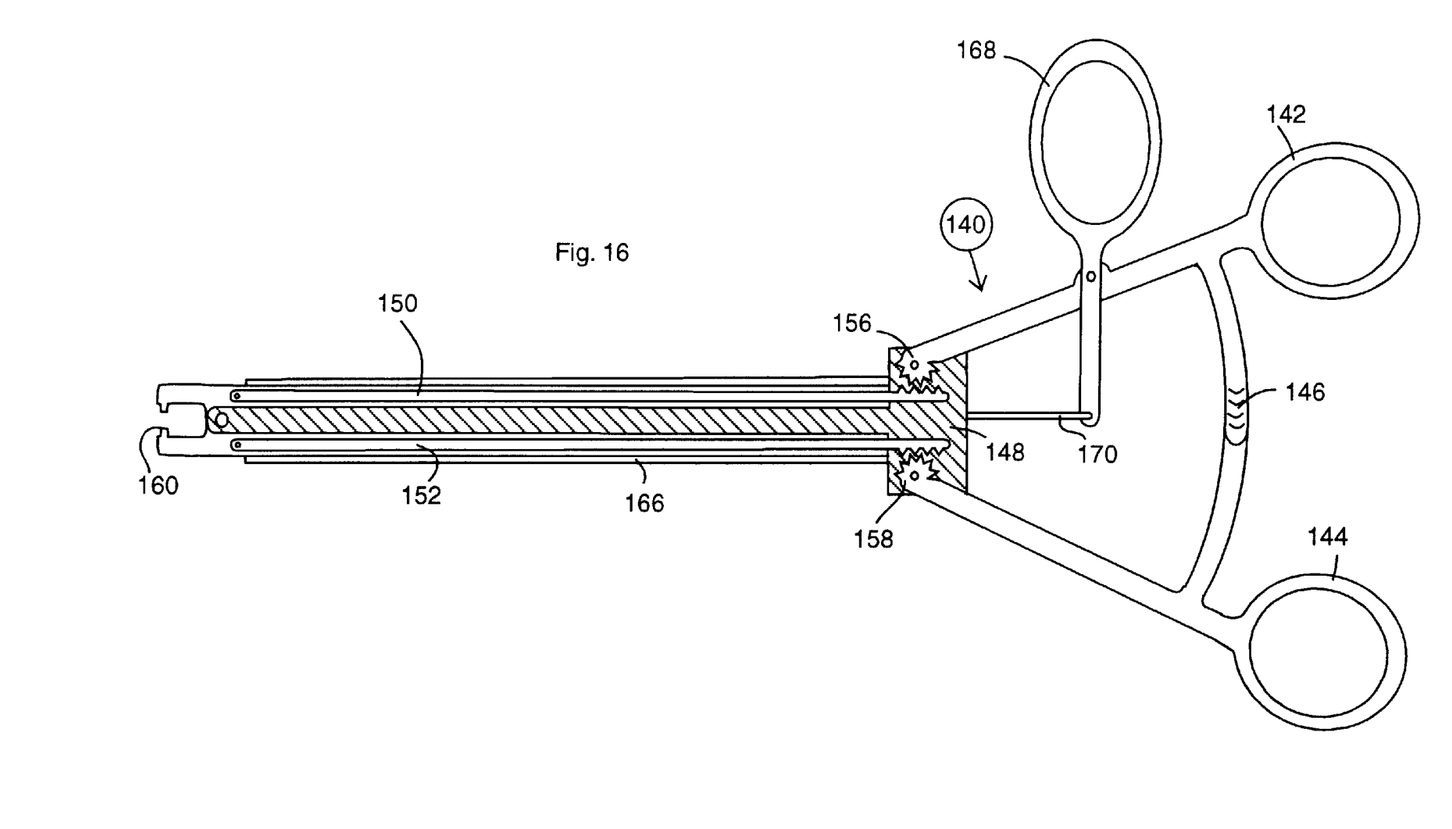
FIG. 16 is a sectional top view of the instrument of FIG. 13.

Similarly, when laproscopic instrument 140 illustrated in FIG. 13 is used with the clamp 100 illustrated in FIG. 10, handle 142 and 144 are opened to the open position, and needle clamp 100 inserted between jaws 158 by pressing arms 106 and 108 toward each other. Pins 160 are inserted into bores 118 and 120, and arms 106 and 108 are allowed to expand to hold clamp 100 on pins 160. Connecting end 114 is pivotally attached to the distal end of manipulator 170. A needle is then inserted between the inner faces of clamp arms 106 and 108, and aligned within needle grooves 122 and 124 with the aid of shoulders 126 and 128.

Handles 142 and 144 are then locked together to close arms 106 and 108 against the needle. Instrument 140 and needle clamp 100 can then be held within sheath 166 and inserted through a trocar into a body cavity. Manipulator 170 can then be pushed forward by pulling on handle 168 to rotate clamp 100 around pins 160, thereby moving the needle along a circular pathway.

Certain modifications and improvements will occur to those skilled in the art upon a reading of the foregoing description. It should be understood that all such modifications and improvements have been deleted herein for the sake of conciseness and readability but are properly within the scope of the follow claims.

What is claimed is:

1. An instrument for holding and manipulating a suturing needle having a given radius of curvature comprising:
   a) a handle having a longitudinal axis, and proximal and distal ends having clamp engaging members; and
   b) a needle clamp having first and second needle clamping arms with inner and outer faces, said clamping arms being moveable between an open position and a closed position, said arms being rotatably supported between said clamp engaging members along a given rotational axis, and having a needle grasping position spaced from said rotational axis, the distance between said rotational axis and said grasping position being approximately equal to the radius of curvature of said needle.

2. The instrument of claim 1, wherein said handle includes first and second opposed clamp engaging members to releasibly hold said needle clamp along an axis of rotation; first and second moveable members having distal ends operatively connected to said clamp engaging members to move said clamp engaging members between open and closed positions, and proximal ends; and a manipulator having a distal end connectable to said needle clamp to rotate said clamp about said axis of rotation.

3. The instrument of claim 1, wherein said clamp engaging members are inwardly directed pins and said clamp includes opposed pin receiving recesses, said pins being insertable into said recesses.

4. The instrument of claim 2, wherein said manipulator is comprised of an elongated member having a distal end rotatably attachable to said needle clamp, and a manipulator handle moveable between retracted and extended positions, said handle being operatively connected to said elongated member, whereby said distal end moves along the longitudinal axis of said instrument to rotate said clamp when said manipulator handle is moved between retracted and extended positions.

5. The instrument of claim 1, further including first and second clamping jaws pivotally attached to the distal ends of said handle, said clamp engaging members projecting inwardly from said jaws, said jaws being pivotal between open and closed positions.

6. The instrument of claim 1, wherein said clamping arms include needle receiving grooves on the inner faces or said arms, said grooves together forming a needle grasping channel when said arms are in their closed position.

7. A needle clamp for use with a handle having a longitudinal axis, and proximal and distal ends to hold and manipulate a suturing needle having a given radius of curvature comprising first and second needle clamping arms with inner and outer faces, and upper and lower edges, said clamping arms being moveable between an open position and a closed position, said arms being rotatably supportable between said handle distal ends along a given rotational axis, and having a needle grasping position spaced from said rotational axis, the distance between said rotational axis and said grasping position being approximately equal to the radius of curvature of said needle.

8. The needle clamp of claim 7, wherein said clamping arms include needle receiving grooves on the inner faces or said arms, said grooves together forming a needle grasping channel when said arms are in their closed position.

9. The needle clamp of claim 7, wherein said clamping arms are substantially parallel to each other.

10. The needle clamp of claim 7, wherein said arms includes needle grasping grooves on the opposite side of said needle grasping position from said rotational axis.

11. The needle clamp of claim 7, wherein said arms include first and second edges, and shoulders projecting outwardly from a corresponding edge of each arm, said shoulders being positioned to support a needle held between said arms at said needle grasping position.

12. The needle clamp of claim 7, wherein one of said arms includes a needle positioning guide extending inwardly from at least one of one of said clamping arms, said guide extending over the corresponding edge of the other clamping arm.

13. The needle clamp of claim 7, further including lever arms extending outwardly from corresponding edges of said arms, said lever arms being joined at a connecting end, said clamp being rotated by moving said connecting end relative to said rotational axis.

14. An instrument for retaining and manipulating a replaceable needle clamp used to clamp a suturing needle having a given radius of curvature, said instrument having a longitudinal axis, said instrument comprising:

a) first and second opposed clamp engaging members to releasibly hold said needle clamp along an axis of rotation;

b) first and second handles having distal ends operatively connected to said clamp engaging members to move said clamp engaging members between open and closed positions, and proximal ends; and c) a manipulator having a distal end releasibly connectable to said needle clamp to rotate said clamp about said axis of rotation.

15. The instrument of claim 14, wherein said clamp engaging member have inwardly directed pins insertable into recesses in said needle clamp, said pins being aligned along said axis of rotation when said clamp is in a closed position.

16. The instrument of claim 14, wherein said handles are generally parallel to each other.

17. The instrument of claim 14, wherein said handles are pivotally connected to each other between their proximal and distal ends.

18. The instrument of claim 14, wherein said manipulator is comprised of an elongated member having a distal end rotatably attachable to said needle clamp, and a manipulator handle moveable between retracted and extended positions, said handle being operatively connected to said elongated member, whereby said distal end moves along the longitudinal axis of said instrument to rotate said clamp when said manipulator handle is moved between retracted and extended positions.

19. The instrument of claim 14, further including first and second clamping jaws pivotally attached to the distal ends of said handles, said clamp engaging member projecting inwardly from said jaws, said jaws being pivotal between open and closed positions.

20. The instrument of claim 14, wherein said needle clamp has an unflexed width, and said clamp engaging members are separated by a first given width when said clamp engaging member is in the open position, said first given width being less than the width of said needle clamp when said clamp is unflexed.

\* \* \* \* \*